US012578338B2

(12) United States Patent
Madabhushi et al.

(10) Patent No.: US 12,578,338 B2
(45) Date of Patent: Mar. 17, 2026

(54) RADIOMIC HETEROGENEITY AS PROGNOSTIC PREDICTOR FOR TREATMENT WITH CDK 4/6 INHIBITORS IN HORMONE RECEPTOR-POSITIVE METASTATIC BREAST CANCER

(71) Applicants: Case Western Reserve University, Cleveland, OH (US); The United States Government as Represented by The Department of Veteran Affairs, Washington, DC (US); The Cleveland Clinic Foundation, Cleveland, OH (US); UH Cleveland Medical Center, Cleveland, OH (US)

(72) Inventors: Anant Madabhushi, Shaker Heights, OH (US); Nathaniel Braman, Bethel Park, PA (US); Siddharth Kunte, Toledo, OH (US); Alberto Montero, Cleveland, OH (US)

(73) Assignees: Case Western Reserve University, Cleveland, OH (US); The United States Government as Represented by The Department of Veteran Affairs, Washington, DC (US); The Cleveland Clinic Foundation, Cleveland, OH (US); UH Cleveland Medical Center, Cleveland, OH (US)

( * ) Notice: Subject to any disclaimer, the term of this patent is extended or adjusted under 35 U.S.C. 154(b) by 1150 days.

(21) Appl. No.: 17/533,458

(22) Filed: Nov. 23, 2021

(65) Prior Publication Data

US 2022/0404364 A1 Dec. 22, 2022

Related U.S. Application Data

(60) Provisional application No. 63/212,216, filed on Jun. 18, 2021.

(51) Int. Cl.
| | | |
|---|---|---|
| *G01N 33/574* | (2006.01) | |
| *G06T 7/00* | (2017.01) | |
(Continued)

(52) U.S. Cl.
CPC ..... *G01N 33/57415* (2013.01); *G06T 7/0012* (2013.01); *G16H 50/20* (2018.01); *G16H 50/30* (2018.01); *G06T 2207/30096* (2013.01)

(58) Field of Classification Search
CPC ......... G06T 7/0012; G06T 2207/20081; G06T 2207/30096; G06T 7/11;
(Continued)

(56) References Cited

U.S. PATENT DOCUMENTS

| | | | | |
|---|---|---|---|---|
| 11,640,661 B2 * | 5/2023 | Washko, Jr. | ........... | G16H 50/30 |
| | | | | 382/131 |
| 2017/0213008 A1 * | 7/2017 | Venn | ...................... | G16H 50/30 |
(Continued)

OTHER PUBLICATIONS

Ganeshan, B., Panayiotou, E., Burnand, K. et al. Tumour heterogeneity in non-small cell lung carcinoma assessed by CT texture analysis: a potential marker of survival. Eur Radiol 22, 796-802 (2012). https://doi.org/10.1007/s00330-011-2319-8 (Year: 2012).*

(Continued)

*Primary Examiner* — John Villecco
*Assistant Examiner* — Courtney Joan Nelson
(74) *Attorney, Agent, or Firm* — Eschweiler & Potashnik, LLC

(57) ABSTRACT

The present disclosure relates to a method of determining a prognostic outlook for patients having metastatic breast cancer. The method includes receiving imaging data from an image of a patient that is receiving or that is to receive cycline dependent kinase 4 and 6 (CDK 4/6) inhibitor therapy for hormone receptor-positive (HR+) metastatic breast cancer. Radiomic heterogeneity features are extracted (Continued)

300 ⟶

Form imaging data set comprising imaging data for patients that are receiving or that are to receive CDK 4/6 inhibitor treatment for HR+ metastatic breast cancer ⟶ 302

Identify lesional masks and perilesional masks of metastases of patients within imaging data set ⟶ 304

Extract radiomic heterogeneity features from lesional masks and from perilesional masks ⟶ 306

Determine radiomic risk scores (RRS) from radiomic heterogeneity features ⟶ 308

Evaluate prognostic performance of RRS ⟶ 310

Arrange patients into different risk groups based upon RRS ⟶ 312 from imaging data associated with a metastasis within the imaging. A prognostic marker is determined from the radiomic heterogeneity features. The prognostic marker is indicative of a response of the patient to CDK 4/6 inhibitor therapy for HR+ metastatic breast cancer.

15 Claims, 9 Drawing Sheets

(51) Int. Cl.
  *G16H 50/20*      (2018.01)
  *G16H 50/30*      (2018.01)
(58) Field of Classification Search
  CPC ... G06T 2207/10056; G06T 7/40; G06T 7/10; G06T 7/45; A61B 8/5223; A61B 6/5205; A61B 6/5217; A61B 5/7275; A61B 2576/00; A61B 5/4312; A61B 8/0825; A61B 5/4842; A61B 5/7264; G06V 2201/03; G06V 10/764; G06V 10/20; G06V 10/761; G06V 20/698; G06V 10/771; G06V 10/806; G06V 10/44; G06V 20/695; G06V 10/25; G16H 50/30; G16H 50/20; G16H 30/40; G16H 50/50; G16H 30/20; G01N 33/574; G01N 33/57415; G01N 2800/52; G06N 3/08; G06N 20/00; G06F 18/211; G06F 18/253; G06F 18/2431
  See application file for complete search history.

(56) References Cited

U.S. PATENT DOCUMENTS

| | | | |
|---|---|---|---|
| 2018/0285531 A1* | 10/2018 | Korn | G16H 50/30 |
| 2019/0019300 A1* | 1/2019 | Simpson | G06T 7/40 |
| 2020/0005931 A1* | 1/2020 | Madabhushi | A61B 5/4381 |
| 2022/0170909 A1* | 6/2022 | Schabath | G01N 33/6827 |

OTHER PUBLICATIONS

Zhao, Yannan, et al. "Prognostic value of tumor heterogeneity on 18F-FDG PET/CT in HR+ HER2-metastatic breast cancer patients receiving 500 mg fulvestrant: a retrospective study." Scientific reports 8.1 (2018): 14458. (Year: 2018).*

Chen, Bihong T., et al. "Predicting survival duration with MRI radiomics of brain metastases from non-small cell lung cancer." Frontiers in Oncology 11 (2021): 621088. (Year: 2021).*

* cited by examiner

100 ⟋▲

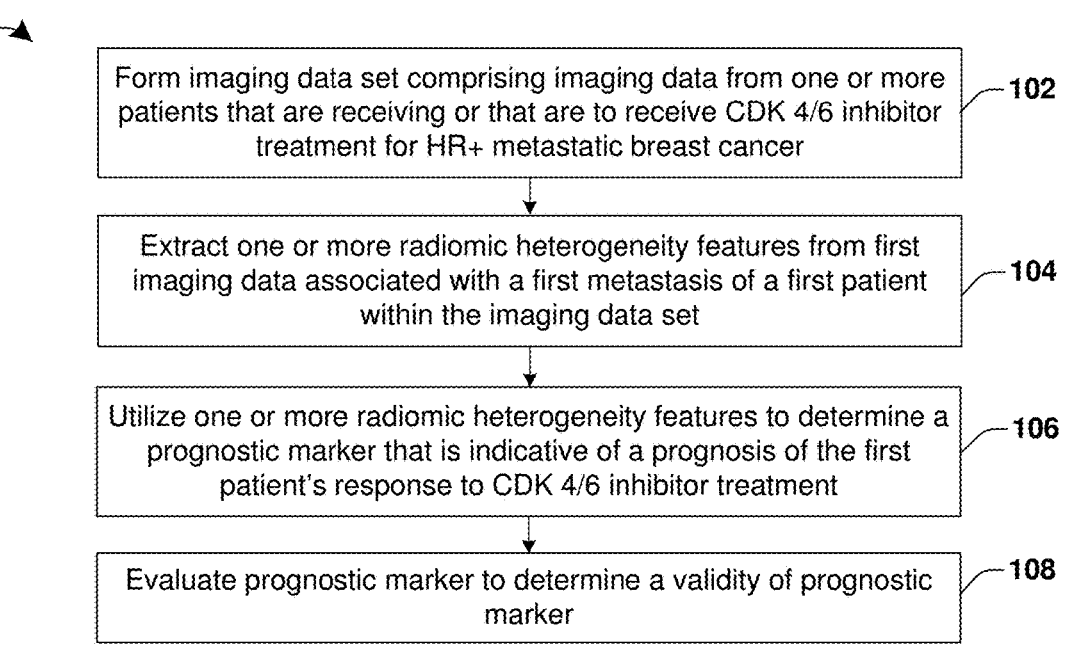

| | |
|---|---|
| Form imaging data set comprising imaging data from one or more patients that are receiving or that are to receive CDK 4/6 inhibitor treatment for HR+ metastatic breast cancer | 102 |
| Extract one or more radiomic heterogeneity features from first imaging data associated with a first metastasis of a first patient within the imaging data set | 104 |
| Utilize one or more radiomic heterogeneity features to determine a prognostic marker that is indicative of a prognosis of the first patient's response to CDK 4/6 inhibitor treatment | 106 |
| Evaluate prognostic marker to determine a validity of prognostic marker | 108 |

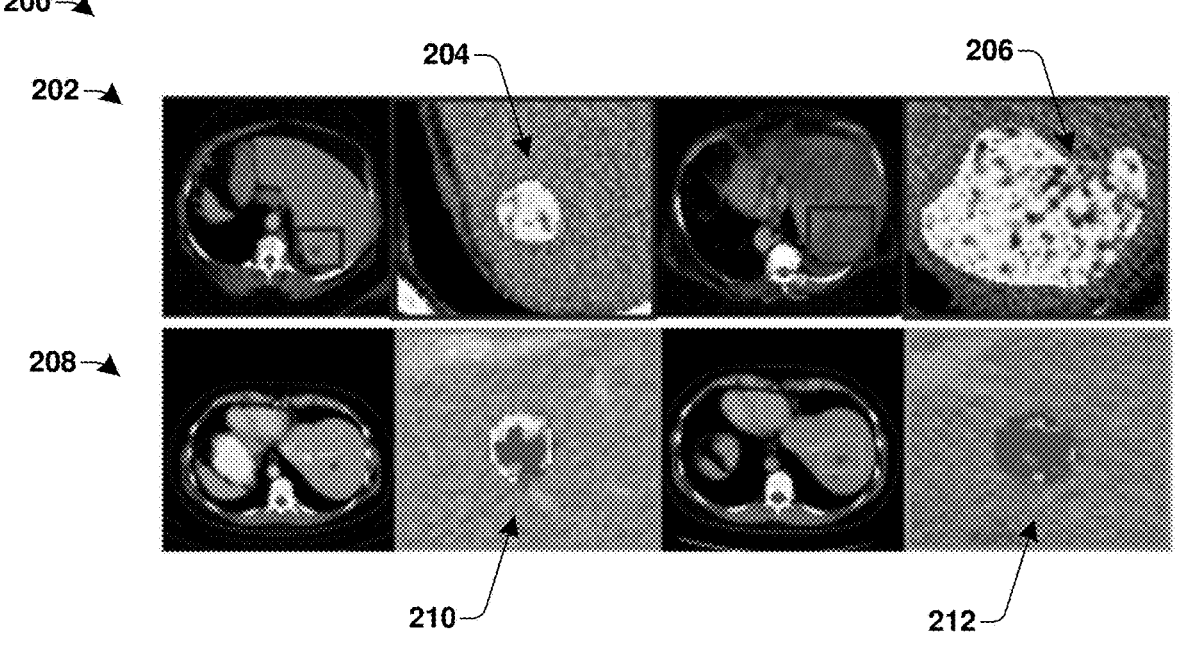

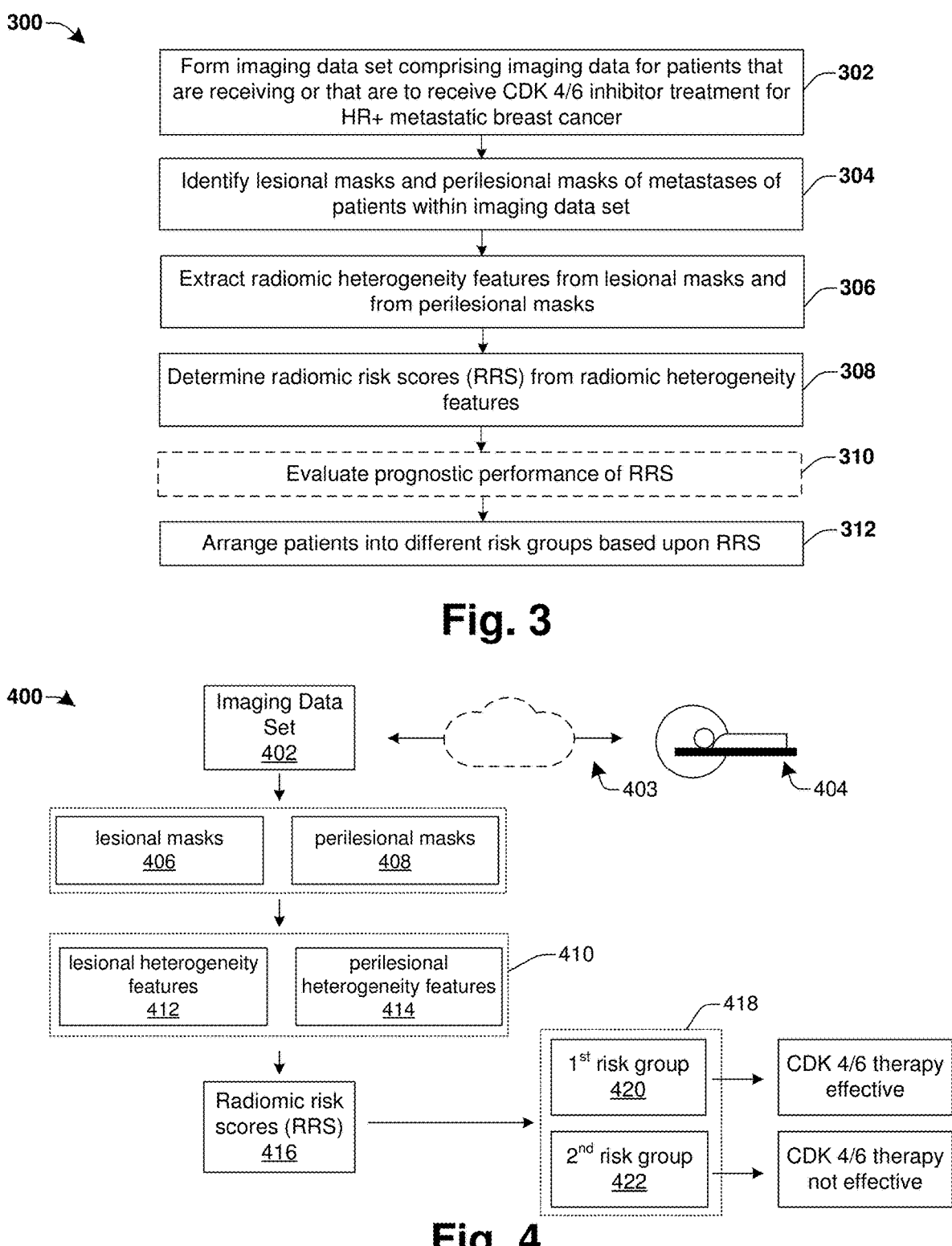

300 ⟍

| | |
|---|---|
| Form imaging data set comprising imaging data for patients that are receiving or that are to receive CDK 4/6 inhibitor treatment for HR+ metastatic breast cancer | 302 |
| Identify lesional masks and perilesional masks of metastases of patients within imaging data set | 304 |
| Extract radiomic heterogeneity features from lesional masks and from perilesional masks | 306 |
| Determine radiomic risk scores (RRS) from radiomic heterogeneity features | 308 |
| Evaluate prognostic performance of RRS | 310 |
| Arrange patients into different risk groups based upon RRS | 312 |

Imaging Data Set
402

403

404 lesional masks
406 perilesional masks
408 lesional heterogeneity features
412 perilesional heterogeneity features
414

410

Radiomic risk scores (RRS)
416

418

1st risk group
420

2nd risk group
422

CDK 4/6 therapy effective

CDK 4/6 therapy not effective

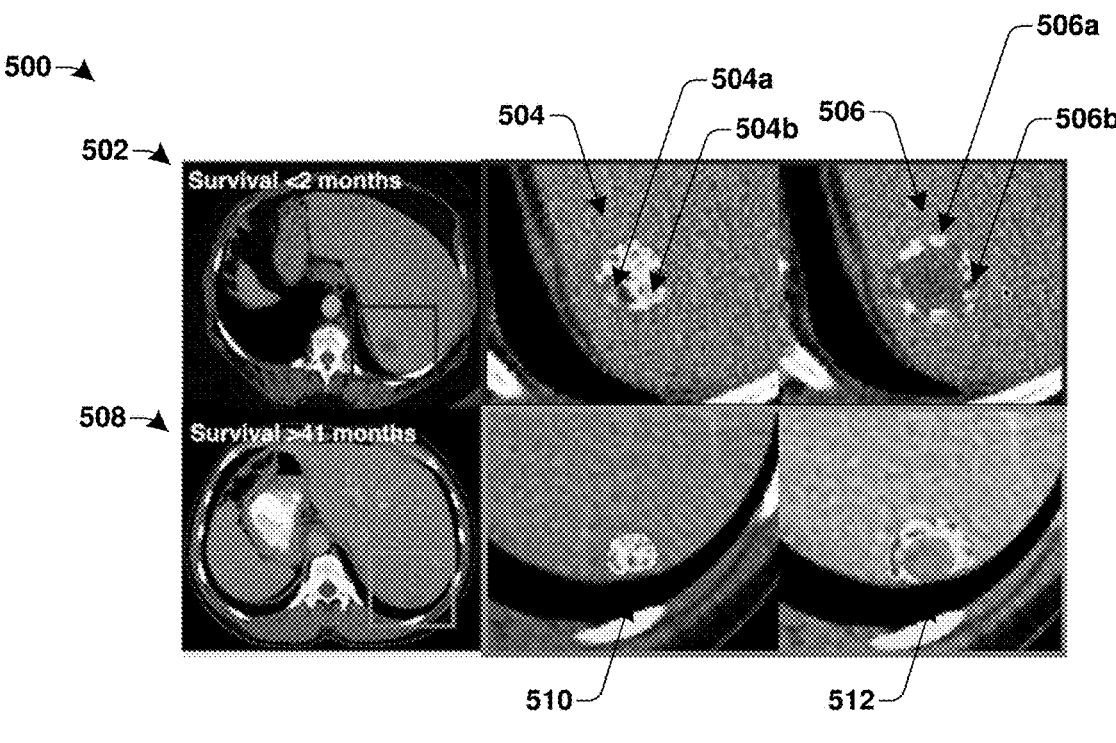

| |
|---|
| Form imaging data set comprising imaging data for patients that are receiving or that are to receive CDK 4/6 inhibitor treatment for HR+ metastatic breast cancer |

─602

| |
|---|
| Extract one or more first radiomic heterogeneity features from pre-treatment image of a metastasis of a patient within imaging data set |

─604

| |
|---|
| Extract one or more second radiomic heterogeneity features from mid-treatment image of the metastasis of the patient within imaging data set |

─606

| |
|---|
| Determine prognostic outcome of patient utilizing one or more first heterogeneity features and one or more second heterogeneity features |

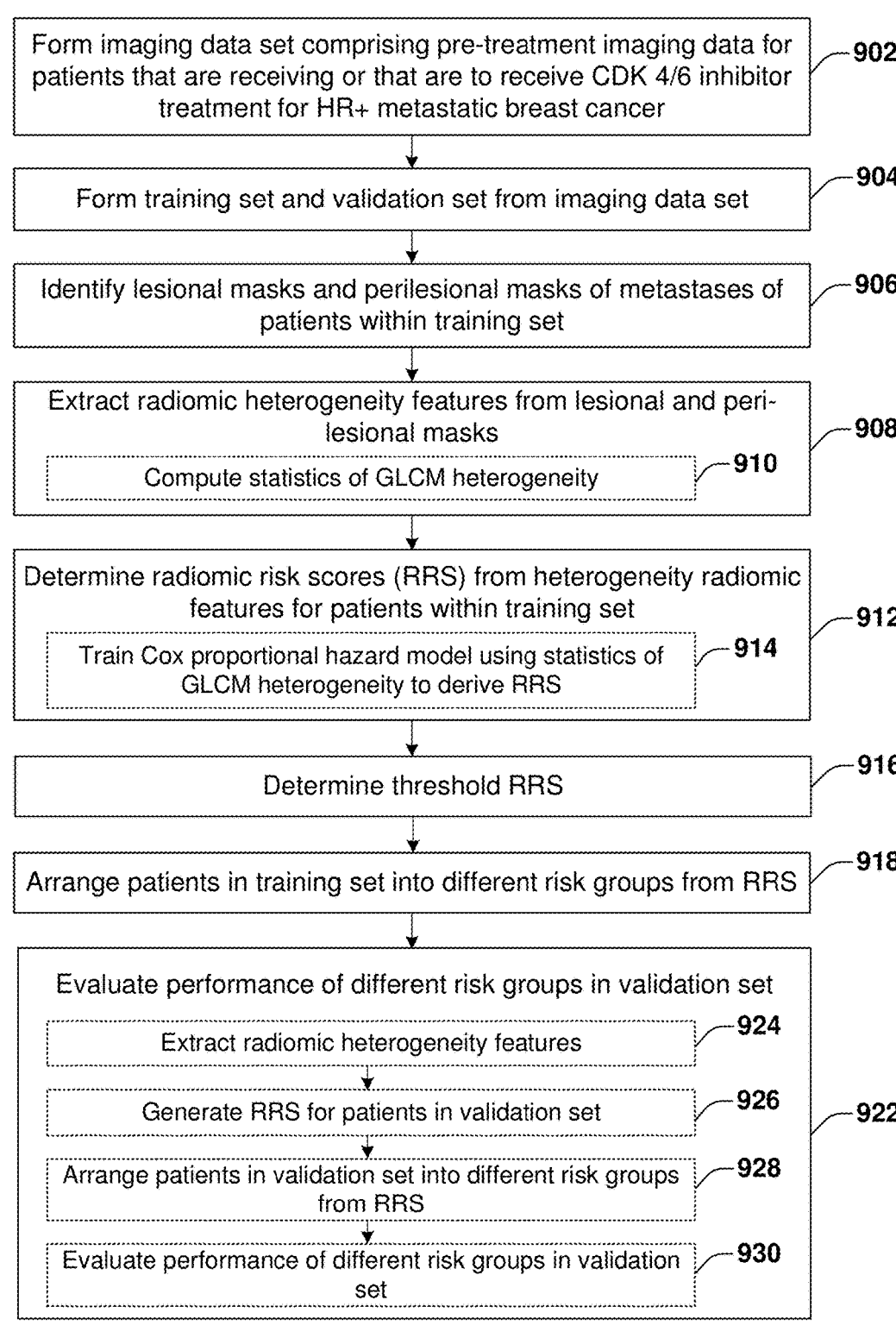

Form imaging data set comprising pre-treatment imaging data for patients that are receiving or that are to receive CDK 4/6 inhibitor treatment for HR+ metastatic breast cancer ⟋902

Form training set and validation set from imaging data set ⟋904

Identify lesional masks and perilesional masks of metastases of patients within training set ⟋906

Extract radiomic heterogeneity features from lesional and peri-lesional masks ⟋908

Compute statistics of GLCM heterogeneity ⟋910

Determine radiomic risk scores (RRS) from heterogeneity radiomic features for patients within training set ⟋912

Train Cox proportional hazard model using statistics of GLCM heterogeneity to derive RRS ⟋914

Determine threshold RRS ⟋916

Arrange patients in training set into different risk groups from RRS ⟋918

Evaluate performance of different risk groups in validation set ⟋922

Extract radiomic heterogeneity features ⟋924

Generate RRS for patients in validation set ⟋926

Arrange patients in validation set into different risk groups from RRS ⟋928

Evaluate performance of different risk groups in validation set ⟋930

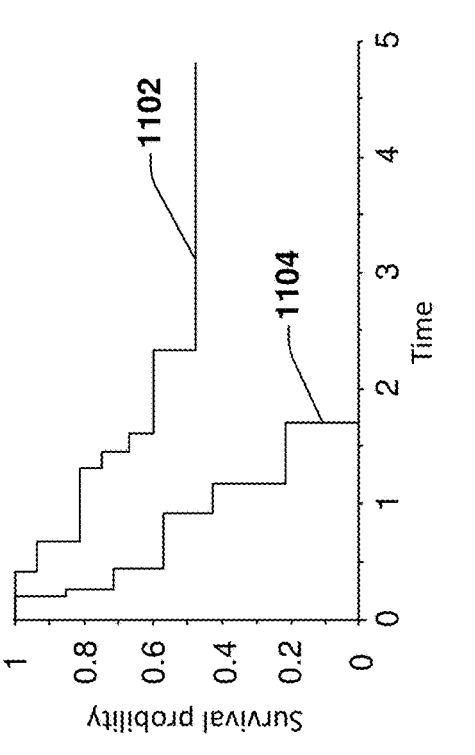
Fig. 11B
Fig. 11A

1200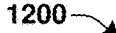

Training

| Form imaging data set comprising imaging data for patients that are receiving or that are to receive CDK 4/6 inhibitor treatment for HR+ metastatic breast cancer | 302 |

| Identify lesional masks and perilesional masks of metastases of patients within imaging data set | 304 |

| Extract radiomic heterogeneity features from lesional masks and from perilesional masks | 306 |

| Determine radiomic risk scores (RRS) from radiomic heterogeneity features | 308 |

| Arrange patients into different risk groups based upon RRS | 312 |

1202

Application

| Receive additional pre-treatment imaging data from additional patient | 1206 |

| Identify additional lesional and peri-lesional masks for additional patient | 1208 |

| Extract additional radiomic heterogeneity features of additional lesional and perilesional masks | 1210 |

| Determine additional radiomic risk score (RRS) from radiomic heterogeneity features | 1212 |

| Classify additional patient into risk group using additional RRS | 1214 |

| Determine treatment plan or additional patient from risk group | 1216 |

RADIOMIC HETEROGENEITY AS PROGNOSTIC PREDICTOR FOR TREATMENT WITH CDK 4/6 INHIBITORS IN HORMONE RECEPTOR-POSITIVE METASTATIC BREAST CANCER

REFERENCE TO RELATED APPLICATION

This application claims the benefit of U.S. Provisional Application No. 63/212,216, filed on Jun. 18, 2021, the contents of which are hereby incorporated by reference in their entirety.

BACKGROUND

Metastatic breast cancer (La, stage 4 breast cancer) is cancer that originated in the breasts, but that has spread to another part of the body (e.g., the liver, brain, bones, lungs, etc.). Metastatic breast cancer is classified as HR-positive if its cells have receptors for the hormones estrogen and progesterone, which suggests the cancer cells receive signals from these hormones that promote their growth.

BRIEF DESCRIPTION OF THE DRAWINGS

The accompanying drawings, which are incorporated in and constitute a part of the specification, illustrate various example operations, apparatus, methods, and other example embodiments of various aspects discussed herein. It will be appreciated that the illustrated element boundaries (e.g., boxes, groups of boxes, or other shapes) in the figures represent one example of the boundaries. One of ordinary skill in the art will appreciate that, in some examples, one element can be designed as multiple elements or that multiple elements can be designed as one element. In some examples, an element shown as an internal component of another element may be implemented as an external component and vice versa. Furthermore, elements may not be drawn to scale.

FIG. 1 illustrates some embodiments of a method of utilizing radiomic heterogeneity features for prognosis of patients with HR+ metastatic breast cancer.

FIG. 2 illustrates exemplary imaging data from radiological scans of liver metastases within patients having HR+ metastatic breast cancer at different times.

FIG. 3 illustrates some embodiments of a method of utilizing radiomic heterogeneity features from imaging data to determine a radiomic risk score (RRS) that can be used for prognosis of patients with HR+ metastatic breast cancer.

FIG. 4 illustrates a block diagram showing some embodiments of a method of utilizing radiomic heterogeneity features from imaging data for prognosis of patients that are receiving or that are to receive CDK 4/6 inhibitor therapy for HR+ metastatic breast cancer.

FIG. 5 illustrates exemplary imaging data from radiological scans of liver metastases within patients having HR+ metastatic breast cancer.

FIG. 6 illustrates some embodiments of a method of utilizing radiomic heterogeneity features from different times for prognosis of patients with HR+ metastatic breast cancer.

FIG. 9 illustrates some embodiments of an additional method of utilizing radiomic heterogeneity features from imaging data for prognosis of patients that are receiving or that are to receive CDK 4/6 inhibitor therapy for HR+ metastatic breast cancer.

FIGS. 11A-11B illustrate exemplary curves showing a survival probability of a plurality of different risk groups of patients receiving CDK 4/6 inhibitor therapy for HR+ metastatic breast cancer.

FIG. 12 illustrates some embodiments of an additional method of utilizing radiomic heterogeneity features from imaging data for prognosis of patients with HR+ metastatic breast cancer.

DETAILED DESCRIPTION

Figures 7, 8A, 8B:
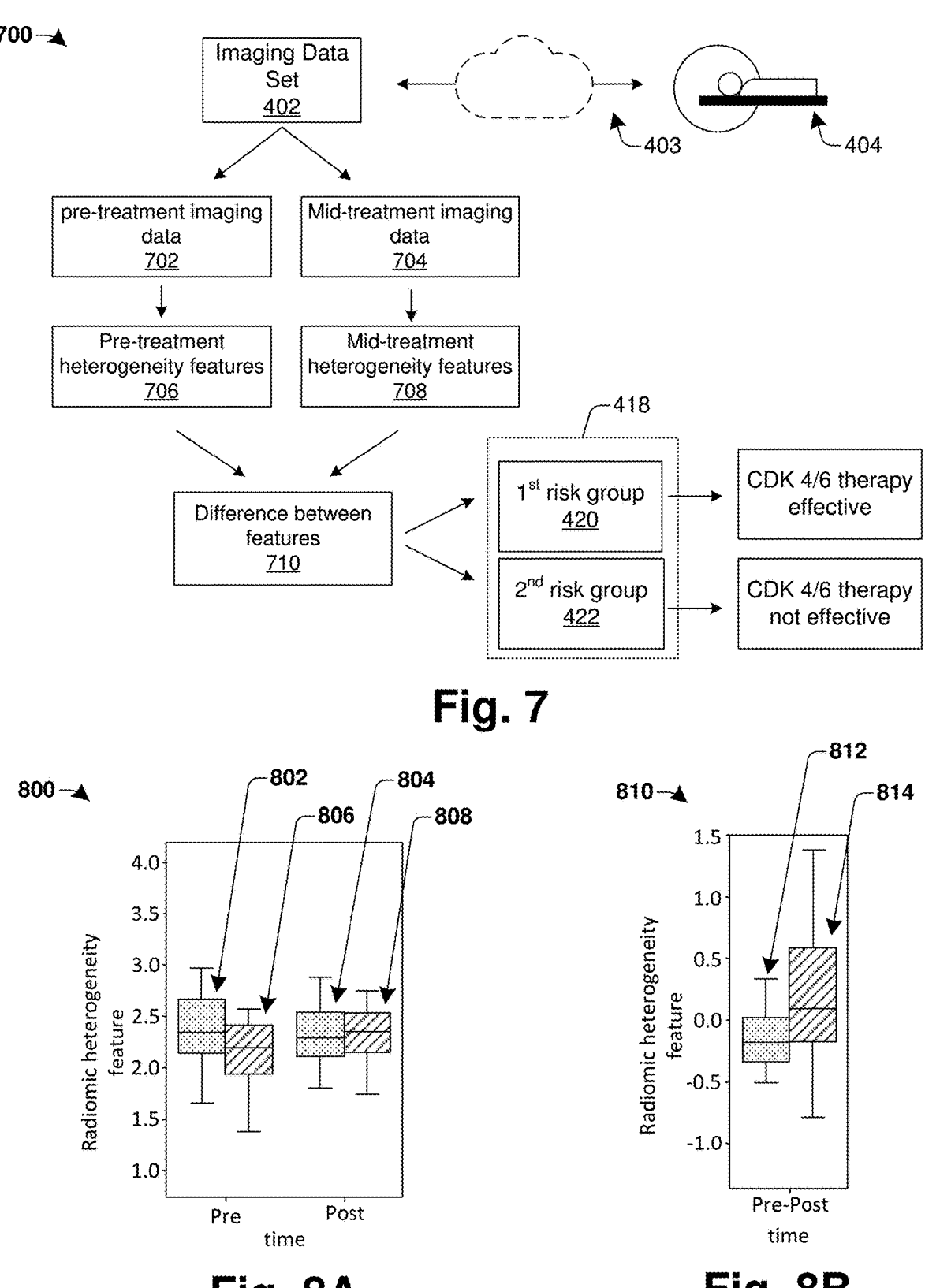
FIG. 7 illustrates a block diagram showing some embodiments of a method of utilizing radiomic heterogeneity features from different times for prognosis of patients that are receiving or that are to receive CDK 4/6 inhibitor therapy for HR+ metastatic breast cancer.
FIG. 8A illustrates a box plot showing examples of radiomic heterogeneity features from different times as a function of survival.
FIG. 8B illustrates a box plot showing examples of a difference between the radiomic heterogeneity features of FIG. 8a as a function of survival.

The description herein is made with reference to the drawings, wherein like reference numerals are generally utilized to refer to like elements throughout, and wherein the various structures are not necessarily drawn to scale. In the following description, for purposes of explanation, numerous specific details are set forth in order to facilitate understanding. It may be evident, however, to one of ordinary skill in the art, that one or more aspects described herein may be practiced with a lesser degree of these specific details. In other instances, known structures and devices are shown in block diagram form to facilitate understanding.

Some types of breast cancer are affected by hormones, such as estrogen and/or progesterone. In such types of breast cancer, the breast cancer cells have receptors (proteins) that attach to estrogen and progesterone, which helps them grow. Endocrine therapy is often used to treat patients having these types of breast cancer after surgery. Recently, endocrine therapy has begun to utilize cyclin-dependent kinases 4/6 (CDK 4/6) inhibitors to stop these hormones from attaching to breast cancer cell receptors and to thereby reduce a risk of the breast cancer returning. CDK 4/6 inhibitors are enzymes that affect cell division in humans. The addition of CDK 4/6 inhibitors to standard endocrine therapy regiments can prevent or delay development of therapeutic resistance when combined with endocrine therapy.

However, almost 20% of patients will not respond to CDK 4/6 inhibitors from the inception of treatment and eventually all and/or nearly all patients will become resistant to CDK 4/6 inhibitors. Additionally, CDK 4/6 inhibitor therapy is very expensive and may cause severe hematological side effects (e.g., neutropenia, agranulocytosis, eosinophilia, thrombocytopenia, purpura, anemia, eukocytosis, thrombocytosis, altered platelet function, or the like) and/or cardiovascular side effects. Studies exploring molecular markers of therapeutic resistance have so far failed to yield a durable marker that indicates a resistance to and/or an effectiveness of treatment with CDK 4/6 inhibitors for patients having HR+ metastatic breast cancer, thereby leaving practitioners with uncertainty over its effectiveness and/or safety as a treatment option for patients.

Accordingly, the present disclosure relates to a method that utilizes radiomic heterogeneity features from imaging data to determine prognostic markers for an effectiveness of CDK 4/6 inhibitor therapy in treating patients having hormone receptor-positive (HR+) metastatic breast cancer. In some embodiments, the method extracts one or more radiomic heterogeneity features from imaging data of a metastasis of a patient having HR+ metastatic breast cancer. It has been appreciated that heterogeneity within a metastasis (e.g., lesion, tumor) and/or outside of the metastasis indicates poor long term patient survival and/or therapeutic response to CDK 4/6 inhibitor therapy. Therefore, the one or more radiomic heterogeneity features may be used to generate a prognostic marker that predicts a response to and/or survival of HR+ metastatic breast cancer patients that receive CDK 4/6 inhibitor therapy. By generating prognostic markers from radiomic heterogeneity features of metastases, an ability of a practitioner to target an effectiveness of CDK 4/6 inhibitor therapy in HR+ metastatic breast cancer patients may be improved, thereby avoiding negative side effects and/or a high cost of the treatment in patients that will not benefit from it.

FIG. 1 illustrates some embodiments of a method 100 of utilizing radiomic heterogeneity features from imaging data to determine a prognosis of patients with HR+ metastatic breast cancer.

At 102, an imaging data set comprising imaging data from one or more patients that are receiving or that are to receive CDK 4/6 inhibitor therapy for HR+ metastatic breast cancer is formed. The imaging data set may be formed using images from a plurality of patients. The imaging data set may comprise imaging data from one or more metastases (e.g., secondary malignant growths or lesions within a liver, brain, lungs, bone, or the like). In some embodiments, the imaging data set comprises pre-treatment imaging data of the one or more patients.

At 104, one or more radiomic heterogeneity features are extracted from first imaging data associated with a first metastasis of a first patient within the imaging data set. The one or more radiomic heterogeneity features are texture features that describe a measure of consistency of signal values (e.g., Hounsfield units) between different points (e.g., pixels, voxels, etc.) within the one or more regions associated with the first metastasis.

At 106, the one or more radiomic heterogeneity features are utilized to determine a prognostic marker that is indicative of a prognosis of the first patient's response to CDK 4/6 inhibitor therapy. In some embodiments, the one or more radiomic heterogeneity features may be input into a machine learning model that is configured to generate the prognostic marker.

At 108, the prognostic marker may be evaluated to determine a validity of the prognostic marker. If the validity of the prognostic marker is found to be poor, determination of the prognostic marker can be re-evaluated (e.g., at 106). For example, in some embodiments if the validity of the prognostic marker is found to be poor, a new prognostic marker can be determined based on different radiomic heterogeneity features of the metastasis. In some embodiments, the prognostic marker may be evaluated as part of a training process of the machine learning model that is used to generate the prognostic marker.

By utilizing method 100 to determine a prognostic marker from radiomic heterogeneity features of a metastasis, imaging data can be used to determine whether or not CDK 4/6 inhibitor therapy will be an effective treatment option in a patient having HR+ metastatic breast cancer, thereby guiding treatment options of a health care provider.

FIG. 2 illustrates exemplary imaging data 200 from radiological scans (e.g., CT scans) of liver metastases within patients having HR+ metastatic breast cancer at different times.

The exemplary imaging data 200 includes imaging data from a first patient 202 that was deceased within a year of initiating CDK 4/6 therapy for treatment of HR+ metastatic breast cancer. The imaging data from the first patient 202 includes images of a first metastasis (e.g., tumor) at a first time 204 before initiating CDK 4/6 therapy and at a second time 206 after initiating CDK 4/6 therapy. The exemplary imaging data 200 further includes imaging data from a second patient 208 that survived for multiple years after initiating CDK 4/6 therapy. The imaging data from the second patient 208 includes images of a second metastasis at a third time 210 before initiating CDK 4/6 therapy and at a fourth time 212 after initiating CDK 4/6 therapy.

The images of the first metastasis at the first time 204 show a higher entropy (e.g., more yellow and red colors) than the images of the second metastasis at the third time 210. The higher entropy is indicative of a higher heterogeneity in the first metastasis at the first time 204 than in the second metastasis at the third time 210. The images of the first metastasis at the second time 206 show that the first metastasis has significantly increased in size. The images of the second metastasis at the fourth time 212 show that the second metastasis has not significantly increased in size. Because the entropy prior to treatment correlates to a change in size of the metastasis while undergoing CDK 4/6 therapy, extracted radiomic heterogeneity features based on entropy may be used to determine a prognostic marker (e.g., as described in method 100 of FIG. 1) that is indicative of an effectiveness of CDK 4/6 therapy to patients having HR+ metastatic breast cancer.

FIG. 3 illustrates some embodiments of a method 300 of utilizing radiomic heterogeneity features from imaging data to determine a radiomic risk score (RRS) that can be used for prognosis of patients with HR+ metastatic breast cancer.

At 302, an imaging data set comprising imaging data for patients that are receiving or that are to receive CDK 4/6 inhibitor therapy for HR+ metastatic breast cancer is formed. The imaging data set may comprise imaging data from metastases (e.g., liver metastases). In some embodiments, the imaging data set comprises or is pre-treatment imaging data.

At 304, lesional masks and perilesional masks are identified for metastases within the imaging data set.

At 306, one or more radiomic heterogeneity features are extracted from one or more regions of respective metastases within the imaging data set. In some embodiments, the one or more radiomic heterogeneity features are extracted from the lesional masks and/or the perilesional masks. In some such embodiments, the one or more radiomic heterogeneity features may comprise one or more lesional radiomic heterogeneity features corresponding to the lesional masks and one or more perilesional radiomic heterogeneity features corresponding to the perilesional masks.

At 308, radiomic risk scores are determined from the one or more radiomic heterogeneity features. The radiomic risk scores are configured to provide a relation between the one or more radiomic heterogeneity features and a prognostic outcome of CDK 4/6 therapy. For example, different radiomic risk scores are indicative of different treatment outcomes for a patient receiving CDK 4/6 therapy for HR+ metastatic breast cancer. In some embodiments, the radiomic risk score may be determined by inputting the one or more lesional radiomic heterogeneity features and the one or more perilesional radiomic heterogeneity features into a machine learning model that is configured to generate the radiomic risk score.

At 310, the radiomic risk scores are evaluated against a prognostic performance of a patient. In various embodiments, the prognostic performance may comprise a change in size of a metastasis, survival rates of patients having the metastases, or the like. In some embodiments, the radiomic risk scores may be evaluated using a survival regression model. In some embodiments, the radiomic risk scores may be evaluated as part of a single process that initially determines the radiomic risk scores (e.g., as part of a training process of a machine learning model comprising a survival regression model).

At 312, the patients are arranged into one of a plurality of different risk groups based on the radiomic risk scores. For example, if a radiomic risk score is low the patient may be placed into a first risk group, while if a radiomic risk score is high the patient may be placed into a second risk group. The plurality of different risk groups respectively correlate to different prognostic treatment outcomes of CDK 4/6 inhibitor therapy.

By generating radiomic risk scores that correlate to a prognosis of treatment of patients within the plurality of different risk groups, an effectiveness of CDK 4/6 inhibitor therapy for a patient can be determined based upon their risk group and/or radiomic risk score. By utilizing the risk group and/or radiomic risk score to determine an effectiveness of CDK 4/6 inhibitor therapy, pre-treatment imaging data can be used to determine whether or not CDK 4/6 inhibitor therapy will be an effective treatment option in a patient having HR+ metastatic breast cancer.

FIG. 4 illustrates a block diagram 400 showing some embodiments of a method of utilizing radiomic heterogeneity features from imaging data for prognosis of patients that are receiving or that are to receive CDK 4/6 inhibitor therapy for HR+ metastatic breast cancer.

As shown in block diagram 400, an imaging data set 402 is formed. The imaging data set 402 comprises imaging data for patients that are receiving or that are to receive CDK 4/6 inhibitor therapy for HR+ metastatic breast cancer. In some embodiments, the imaging data set 402 may comprise imaging data of metastases in patients having HR+ metastatic breast cancer and available pre-treatment imaging data. In some embodiments, the imaging data set 402 may comprise imaging data of liver metastases.

In some embodiments, the imaging data within the imaging data set 402 may be obtained directly from one or more imaging tools 404. In additional embodiments, the imaging data within the imaging data set 402 may be obtained from an on-line data base 403. In various embodiments, the imaging data may comprise data from a radiological image. For example, the imaging data may comprise data from an x-ray, a computerized tomography (CT) scan, a magnetic resonance imaging (MRI) scan, nuclear imaging, positron emission tomography (PET) scan, a CT/PET scan, an ultrasound, or the like.

The imaging data set 402 is used to generate lesional masks 406 and perilesional masks 408. In some embodiments, the lesional masks 406 may be formed by removing imaging data relating to parts of an image that are around a metastasis, so that the lesional masks 406 predominately have intra-lesional data within metastases. Similarly, the perilesional masks 408 may be formed by removing data relating to parts of an image that are within a metastasis, so that the perilesional masks 408 predominately have data relating to a region around metastases.

Radiomic heterogeneity features 410 are extracted from each of the lesional masks 406 and the perilesional masks 408. For example, a first plurality of radiomic heterogeneity features are extracted from a first lesional mask and a first perilesional mask, a second plurality of radiomic heterogeneity features are extracted from a second lesional mask and a second perilesional mask, etc. In some embodiments, the radiomic heterogeneity features 410 may comprise lesional radiomic heterogeneity features 412 extracted from the lesional masks 406 and perilesional radiomic heterogeneity features 414 extracted from the perilesional masks 408. In various embodiments, the radiomic heterogeneity features 410 may comprise Laws Energy Measures, Local Binary Pattern, Gabor wavelets, Co-occurrence of Local Anisotropic Gradient Orientations, gray level run length matrix, gray level size zone matrix, gray level dependence matrix, neighboring gray tone difference matrix, and/or first order statistics of intensity values.

In some embodiments, the radiomic heterogeneity features 410 may be determined by measuring variations (e.g., grayscale intensity variations) between pixels or voxels within regions (e.g., a lesional mask, a perilesional mask) of an image defined by the imaging data set, by measuring entropy in the image, or the like. In some embodiments, the radiomic heterogeneity features 410 may be determined by measuring difference in intensity units (e.g., attenuation, measured in Hounsfield units) between pixels or voxels within the lesional masks 406 and the perilesional masks 408. Heterogeneity features may be measured directly on the image itself, or on a derived variation of the image produced by first applying one or more filters (e.g. wavelet decomposition, Laplace of gradient, square or logarithm of intensity values).

In some additional embodiments, the radiomic heterogeneity features 410 may be extracted using a gray level co-occurrence matrix (GLCM). In such embodiments, the GLCM may measure heterogeneity by determining a distribution of co-occurring pixel values (e.g., Hounsfield units) at a given offset, so as to determine how closely image signals within a local region are and thus give a measure of heterogeneity within the lesional masks 406 and the perilesional masks 408. In some embodiments, the statistics of GLCM heterogeneity comprise a matrix that is defined over the lesional masks 406 and the perilesional masks 408.

In some additional embodiments, the radiomic heterogeneity features 410 may respectively be determined by computing a GLCM metric for a plurality of pixels within the lesional masks 406 and/or the perilesional masks 408 and subsequently applying a statistical technique to the GLCM metrics for the plurality of pixels. For example, an entropy may be determined for a plurality of pixels within a perilesional mask, and a mean of the entropy may be determined for the plurality of pixels to determine a first radiomic heterogeneity feature. In various embodiments, the GLCM metrics may comprise entropy, energy, contrast, homogeneity, prominence, and/or the like. In various embodiments, the statistical techniques may comprise a mean, a medium, a standard deviation, a skewness, etc. In some embodiments, the lesional radiomic heterogeneity features 412 may comprise a statistical measure of a GLCM metric measured on a lesional mask and the perilesional radiomic heterogeneity features 414 may comprise a statistical measure of a GLCM metric measured on a perilesional mask. Some non-limiting examples of the radiomic heterogeneity features may include a first radiomic heterogeneity feature comprising a median value of GLCM entropy within a lesional mask, a second radiomic heterogeneity feature comprising a standard deviation of GLCM contrast within a perilesional mask, etc.

Radiomic risk scores (RRS) 416 may be determined from the radiomic heterogeneity features 410. For example, a first RRS may be determined from radiomic heterogeneity features associated with a metastasis of a first patient, a second RRS may be determined from radiomic heterogeneity features associated with a metastasis of a second patient, etc. In some embodiments the RRS 416 may be determined using a machine learning model comprising a survival regression model that utilizes the radiomic heterogeneity features 410 to determine the RRS 416 based upon a survival time of patients. In such embodiments, the RRS 416 may correspond to the survival time (e.g., a high survival time may indicate a low RRS score and a low survival time may indicate a high RRS score). In some embodiments, the survival regression model may comprise a Cox proportional hazards model or an elastic net regularized Cox proportional hazards model that is trained using the statistics of GLCM heterogeneity to derive the RRS 416. The survival prediction may be utilized to rank patients by the time until death ("Overall survival"), or time until an escalation of disease severity, for instance progression ("progression-free survival") or recurrence ("recurrence-free survival"), or other similar metrics. In other embodiments, the RRS may be determined by training a classification model to predict discrete outcome-related groups (e.g. response vs. non-response, or survival greater than a year vs. survival less than a year). This classification model may comprise for example statistical classifiers such as a logistic regression, random forest, linear discriminant analysis, or support vector machine model and may also comprise a fully connected neural network with one or more hidden layers. In these cases, the output probability of risk-associated class membership would constitute the RRS. Furthermore, the unaltered values of one or more heterogeneity features could be utilized as the RRS, if they are themselves associated with directly with survival or therapeutic outcome.

In some embodiments, the RRS 416 may be determined from both lesional radiomic heterogeneity features 412 and perilesional radiomic heterogeneity features 414. For example, the RRS 416 may be respectively determined from a first number of the lesional radiomic heterogeneity features 412 (e.g., 2 lesional radiomic heterogeneity features) and a second number of the perilesional radiomic heterogeneity features 414 (e.g., 3 perilesional radiomic heterogeneity features). In some embodiments, the first number of lesional radiomic heterogeneity features 412 may be a different number than the second number of perilesional radiomic heterogeneity features 414, while in other embodiments the first number of lesional radiomic heterogeneity features 412 may be a same number as the second number of perilesional radiomic heterogeneity features 414. In some embodiments, the lesional radiomic heterogeneity features 412 may comprise a median value of GLCM entropy within a lesional mask, a mean value of GLCM entropy within a lesional mask, or the like. In some embodiments, the perilesional radiomic heterogeneity features 414 may comprise a skewness of GLCM entropy within a perilesional mask, a kurtosis of GLCM entropy within a perilesional mask, or the like.

Patients are arranged into a plurality of different risk groups 418 based on their RRS 416. For example, patients having a RRS 416 that is below a threshold may be grouped into a first risk group 420, while patients having a RRS 416 that is above the threshold may be grouped into a second risk group 422. The first risk group 420 is indicative of patients that will likely respond well to CDK 4/6 therapy as a treatment option for HR+ metastatic breast cancer (e.g., that will have a 1 year survival rate of over 50%). The second risk group 422 is indicative of patients that will likely respond poorly to CDK 4/6 therapy as a treatment option for HR+ metastatic breast cancer (e.g., that will have a 1 year survival rate of less than 50%).

FIG. 5 illustrates exemplary imaging data 500 from radiological scans (e.g., CT scans) of liver metastases within patients having HR+ metastatic breast cancer.

The exemplary imaging data 500 includes first imaging data 502 of a first liver metastasis from a first patient having HR+ metastatic breast cancer. The first patient survived for a relatively short first time (e.g., less than approximately two months) after initiating CDK 4/6 inhibitor therapy. In the first imaging data 502, a square surrounds a first region of tissue having the first liver metastasis. From the first imaging data 502, a first lesional mask 504 is formed and a first perilesional mask 506 is formed.

Radiomic heterogeneity features of both the first lesional mask 504 and the first perilesional mask 506 are determined. In some embodiments, the radiomic heterogeneity features may be determined by measuring an entropy at different points within the first lesional mask 504 and the first perilesional mask 506. In the first lesional mask 504 and the first perilesional mask 506, warm colored regions 504a/506a (e.g., red and orange regions) indicate a high level of entropy, while cool colored regions 504b/506b (e.g., yellow, green, and blue regions) indicate a lower level of entropy. Since the first lesional mask 504 and the first perilesional mask 506 both contain a high degree of warm colored regions 504a/506a, the entropy indicates a high degree of textural heterogeneity, thereby indicating more disordered tissue type. The higher levels of textural heterogeneity within the first liver metastasis and the surrounding perilesional region corresponds with a high RRS score that is indicative of poor survival and thus poor treatment outcome for the first patient in response to CDK 4/6 therapy.

The exemplary imaging data further includes second imaging data 508 of a second liver metastasis from a second patient having HR+ metastatic breast cancer. The second patient survived for a second time (e.g., greater than or equal to approximately 41 months), which was longer than the first time, after initiating CDK 4/6 inhibitor therapy. In second imaging data 508, a square surrounds a second region of tissue having the second liver metastasis. From the second imaging data 508, a second lesional mask 510 is formed and a second perilesional mask 512 is formed. Since the second lesional mask 510 and the second perilesional mask 512 both contain a low degree of warm colored regions, the entropy indicates a low degree of textural heterogeneity, thereby indicating less disordered tissue type. The low levels of textural heterogeneity within the second liver metastasis and surrounding perilesional region corresponds with a low RRS score that is indicative of a high likelihood of success for CDK 4/6 therapy of the second patient.

FIG. 6 illustrates some embodiments of a method 600 of utilizing radiomic heterogeneity features from pre-treatment and mid-treatment imaging data for prognosis of patients with HR+ metastatic breast cancer.

At 602, an imaging data set comprising imaging data for patients that are receiving or that are to receive CDK 4/6 inhibitor therapy for HR+ metastatic breast cancer is formed. In some embodiments, the imaging data set may comprise imaging data from metastases (e.g., liver metastases).

At 604, one or more first radiomic heterogeneity features are extracted from one or more regions of a metastasis of a patient within a pre-treatment image within the imaging data set. The pre-treatment image of the metastasis is an image taken before CDK 4/6 inhibitor therapy has begun.

At 606, one or more second radiomic heterogeneity features are extracted from one or more regions of the metastasis of the patient within a mid-treatment image within the imaging data set. The mid-treatment image of the metastasis is an image taken after CDK 4/6 inhibitor therapy has begun.

At 608, a prognostic outcome of the patient having the metastasis is determined from the one or more first radiomic heterogeneity features and the one or more second radiomic heterogeneity features. In some embodiments, the prognostic outcome may be determined based upon a difference between the one or more first radiomic heterogeneity features and the one or more second radiomic heterogeneity features. The prognostic outcome can be used to determine an effectiveness of CDK 4/6 inhibitor therapy for the patient.

FIG. 7 illustrates a block diagram 700 showing some embodiments of a method of utilizing radiomic heterogeneity features from pre-treatment and mid-treatment imaging data for prognosis of patients with HR+ metastatic breast cancer.

As shown in block diagram 700, an imaging data set 402 is formed. The imaging data set 402 comprises imaging data from patients that are receiving CDK 4/6 inhibitor therapy for HR+ metastatic breast cancer. In some embodiments, the imaging data set 402 may comprise imaging data of metastases in patients having HR+ metastatic breast cancer and available pre-treatment imaging data. In some embodiments, the imaging data set 402 may comprise imaging data of liver metastases. In some embodiments, the imaging data within the imaging data set 402 may be obtained directly from one or more imaging tools 404. In other embodiments, the imaging data within the imaging data set 402 may be obtained from an on-line data base 403.

The imaging data set 402 is split into pre-treatment imaging data 702 and mid-treatment imaging data 704. The pre-treatment imaging data 702 comprises data corresponding to a metastasis prior to a patient receiving CDK 4/6 therapy, while the mid-treatment imaging data 704 comprises data corresponding to the metastasis after the patient receives CDK 4/6 therapy.

One or more pre-treatment radiomic heterogeneity features 706 are extracted from the pre-treatment imaging data 702 and one or more mid-treatment radiomic heterogeneity features 708 are extracted from the mid-treatment imaging data 704. In some embodiments, the one or more pre-treatment radiomic heterogeneity features 706 and the one or more mid-treatment radiomic heterogeneity features 708 may be determined using a gray level co-occurrence matrix (GLCM).

A difference 710 between the one or more pre-treatment radiomic heterogeneity features 706 and the one or more mid-treatment radiomic heterogeneity features 708 is determined. The difference between the one or more pre-treatment radiomic heterogeneity features 706 and the one or more mid-treatment radiomic heterogeneity features 708 may be determined by subtracting the one or more mid-treatment radiomic heterogeneity features 708 from the one or more pre-treatment radiomic heterogeneity features 706.

In some embodiments, patients are arranged into a plurality of different risk groups 418 based on their difference 710 between the one or more pre-treatment radiomic heterogeneity features 706 and the one or more mid-treatment radiomic heterogeneity features 708. For example, patients having a difference 710 that is below a threshold may be grouped into a first risk group 420, while patients having a difference 710 that is above the threshold may be grouped into a second risk group 422. The first risk group 420 is indicative of patients that will likely respond well to CDK 4/6 therapy as a treatment option for HR+ metastatic breast cancer (e.g., that will have a 1 year survival rate of over 50%). The second risk group 422 is indicative of patients that will likely respond poorly to CDK 4/6 therapy as a treatment option for HR+ metastatic breast cancer (e.g., that will have a 1 year survival rate of less than 50%).

FIG. 8*a* illustrates a box plot 800 showing examples of radiomic heterogeneity features from different times in relation to survival.

Box plot 800 shows first radiomic heterogeneity features extracted from a first metastasis of a first patient at a first pre-treatment time 802 that occurs prior to the first patient receiving CDK 4/6 therapy and at a first mid-treatment time 804 that occurs after the first patient receives CDK 4/6 therapy. Box plot 800 also shows second radiomic heterogeneity features extracted from a second metastasis of a second patient at a second pre-treatment time 806 that occurs prior to the second patient receiving CDK 4/6 therapy and at a second mid-treatment time 808 that occurs after the second patient receives CDK 4/6 therapy. The first patient survived for a longer time than the second patient.

FIG. 8*b* illustrates a box plot 810 showing examples of a difference between the radiomic heterogeneity features of FIG. 8*a* in relation to survival.

Box plot 810 illustrates a difference between the radiomic heterogeneity features at the pre-treatment times and at the post-treatment times. A first difference 812 between the first heterogeneity features at the first pre-treatment time 802 and the first mid-treatment time 804 is relatively small (e.g., less than or equal to approximately 0), thereby indicating a small growth of the first metastasis. This is consistent with the survival of the first patient and thus indicates a good correlation between a response to CDK 4/6 inhibitor therapy and a difference between the first heterogeneity features at the first pre-treatment time 802 and the first mid-treatment time 804

However, a second difference 814 between the second heterogeneity features at the second pre-treatment time 806 and the second mid-treatment time 808 is relatively large (e.g., greater than or equal to approximately 0), thereby indicating a growth of the second metastasis. This is consistent with the death of the second patient and thus indicates a good correlation between a response to CDK 4/6 inhibitor therapy and a difference between the second heterogeneity features at the second pre-treatment time 806 and the second mid-treatment time 808. Because the differences between heterogeneity features at different times correlate to survival of a patient, extracted radiomic heterogeneity features may be used to determine a prognostic marker (e.g., as described in method 100 of FIG. 8) that is indicative of an effectiveness of CDK 4/6 therapy to patients having HR+ metastatic breast cancer.

FIG. 9 illustrates some embodiments of an additional method 900 of utilizing radiomic heterogeneity features from pre-treatment imaging data for prognosis of patients that are receiving or that are to receive CDK 4/6 inhibitor therapy for HR+ metastatic breast cancer.

While the disclosed methods (e.g., methods 100, 300, 600, 900, and 1200) are illustrated and described herein as a series of acts or events, it will be appreciated that the illustrated ordering of such acts or events are not to be interpreted in a limiting sense. For example, some acts may occur in different orders and/or concurrently with other acts or events apart from those illustrated and/or described herein. In addition, not all illustrated acts may be required to implement one or more aspects or embodiments of the description herein. Further, one or more of the acts depicted herein may be carried out in one or more separate acts and/or phases.

At 902, an imaging data set comprising pre-treatment imaging data for patients having HR+ metastatic breast cancer is formed.

At 904, the imaging data set is separated into a training set and a validation set.

At 906, lesional masks and perilesional masks are identified for metastases of patients within the training set.

At 908, lesional and perilesional radiomic heterogeneity features are extracted from the one or more lesional masks and the one or more perilesional masks, respectively. In some embodiments, the radiomic heterogeneity features may be extracted using GLCM heterogeneity measurements, at 910.

At 912, a radiomic risk score (RRS) is determined from the lesional and perilesional radiomic heterogeneity features. In some embodiments, the radiomic risk score may be determined by using a machine learning model comprising a Cox proportional hazard model, at 914.

At 916, a radiomic risk score threshold (RRS threshold) is determined.

At 918, patients are arranged into a plurality of different risk groups based on their RRS. For example, patients having a RRS that is greater than or equal to the RRS threshold may be grouped into a first risk group, while patients having a RRS that is less than the RRS threshold may be grouped into a second risk group.

At 922, a prognostic performance of patients within the plurality of different risk groups in the validation set is evaluated. In various embodiments, the prognostic performance of the plurality of different risk groups may be determined according to acts 924-930.

At 924, radiomic heterogeneity features are extracted from imaging data of metastases of patients within the validation set.

At 926, RRS are generated from the radiomic heterogeneity features from patients in the validation set.

At 928, the patients in the validation set are grouped into a plurality of different risk groups based on their RRS.

At 930, a prognostic performance of patients within the plurality of different risk groups is evaluated. In various embodiments, the prognostic performance may comprise change in size of a metastasis, a number of metastases, survival, or the like. For example, in some embodiments, the prognostic performance may determine a survival rate (e.g., a 1 year survival rate, a 5 year survival rate, or the like) for patients that are receiving CDK 4/6 inhibitor therapy within the first risk group and within the second risk group.

Figure 10:
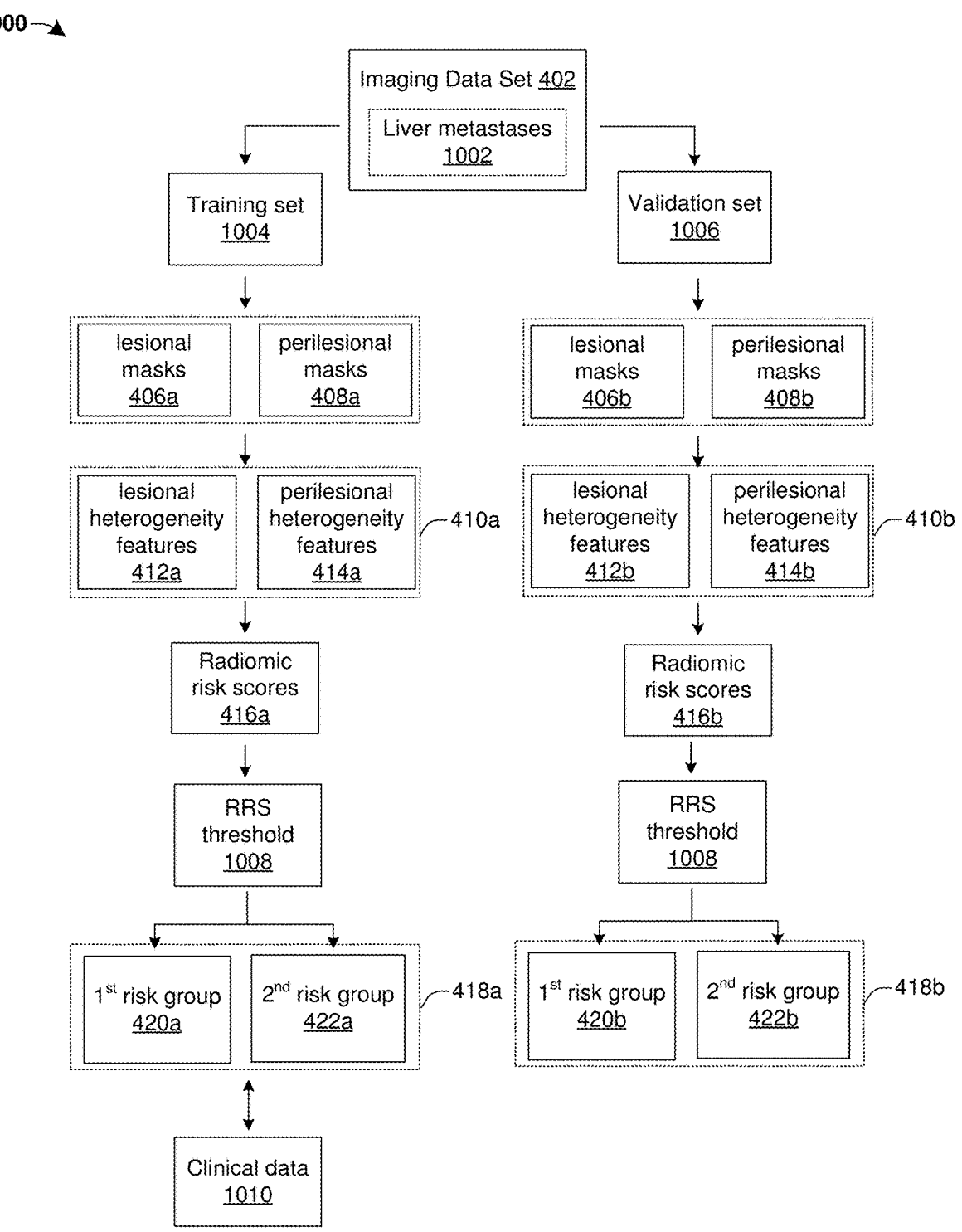
FIG. 10 illustrates a block diagram showing some additional embodiments of a method of utilizing radiomic heterogeneity features from imaging data for prognosis of patients that are receiving or that are to receive CDK 4/6 inhibitor therapy for HR+ metastatic breast cancer.

FIG. 10 illustrates a block diagram 1000 showing some additional embodiments of a method of utilizing radiomic heterogeneity features from imaging data for prognosis of patients that are receiving or that are to receive CDK 4/6 inhibitor therapy for HR+ metastatic breast cancer.

As shown in block diagram 1000, an imaging data set 402 is formed. The imaging data set 402 comprises imaging data for patients that are receiving or that are to receive CDK 4/6 inhibitors (e.g., palbociclib and endocrine therapy) for HR+ metastatic breast cancer. In some embodiments, the imaging data set 402 comprises imaging data of metastases (e.g., liver metastasis 1002). In some embodiments, the imaging data set 402 may comprise data from responders (e.g., patients that had an objective response and/or stable disease per RECISTS (Response evaluation criteria in solid tumors) v1.1, for a response during of greater than or equal to approximately 6 months) and non-responders (e.g., patients that had no progression of disease within 6 months).

In some embodiments, the imaging data set may be formed by taking data from a first plurality of patients that have metastatic HR+ breast cancer and are receiving CDK 4/6 inhibitor therapy. The first plurality of patients may be reduced to a second plurality of patients that also have liver metastases and then further reduced to a third plurality of patients that also have confirmed liver metastases prior to treatment.

The imaging data set 402 may be randomly divided into a training set 1004 comprising data from a first group of the plurality of patients and a validation set 1006 (i.e., a testing set) comprising data from a second group of the plurality of patients.

The training set 1004 is used to generate lesional masks 406a and perilesional masks 408a. In some embodiments, the metastases within the imaging data may be manually delineated (e.g., contoured) and used to generate the lesional masks 406a and the perilesional masks 408a. In some embodiments, the perilesional masks 408a may comprise liver tissue that surrounds the metastases. In some embodiments, the perilesional masks 408a may have a width of approximately 5 mm surrounding an associated metastasis. In others embodiments, the perilesional masks 408a may have a width of approximately 10 mm, approximately 15 mm, or other similar values, surrounding an associated metastasis.

Radiomic heterogeneity features 410a are extracted from each of the lesional masks 406a and the perilesional masks 408b. In some embodiments, the radiomic heterogeneity features 410a may comprise lesional radiomic heterogeneity features 412a and perilesional radiomic heterogeneity features 414a. In some embodiments, radiomic heterogeneity features 410a may be determined using a gray level co-occurrence matrix (GLCM). The GLCM measures heterogeneity by measuring how closely associated image signals within a local region are, thereby giving a measure of heterogeneity within a metastasis and outside a metastasis. In some embodiments, the heterogeneity measured by the GLCM may comprise a matrix that is defined over the lesional masks 406a and the perilesional masks 408a.

From the radiomic heterogeneity features 410a, radiomic risk scores (RRS) 416a may be determined. In some embodiments, the RRS 416a may be determined from both lesional radiomic heterogeneity features 412a and perilesional radiomic heterogeneity features 414a, since these features are elevated in patients with poor post treatment survival.

In some embodiments, using the statistics of GLCM heterogeneity, an elastic net regularized Cox proportional hazards model may be trained to derive the RRS 416a. In such embodiments, the elastic net regularized Cox proportional hazards model may be trained by comparing an output of the model (e.g., overall survival (OS)) to actual results of patients in the training set until a good correlation is achieved. In some such embodiments, a RRS threshold 1008 may also be derived from the RRS 416a determined using the training set.

Individual ones of the RRS 416a may be compared to the RRS threshold to stratify patients within a plurality of different risk groups 418a. For example, individual patients having an RRS that is below the RRS threshold 1008 may be placed into a first risk group 420a that is indicative of a positive outcome for patients receiving CDK 4/6 therapy, while individual patients having an RRS that is above the RRS threshold 1008 may be placed into a second risk group 422a that is indicative of a negative outcome for patients receiving CDK 4/6 therapy.

The validation set 1006 (e.g., a testing set) may be subsequently used to evaluate a performance of the plurality of different risk groups 418a determined by the training set 1004. In such embodiments, lesional masks 406b and perilesional masks 408b are formed from the validation set 1006. Radiomic heterogeneity features 410b are extracted from the lesional masks 406b and the perilesional masks 408b. The radiomic heterogeneity features 410b include lesional radiomic heterogeneity features 412b extracted from the lesional masks 406a and perilesional radiomic heterogeneity features 414b extracted from the perilesional masks 408b. Radiomic risk scores 416b are determined from the lesional radiomic heterogeneity features 412b and perilesional radiomic heterogeneity features 414b. The RRS 416b are compared to the RRS threshold 1008 to determine placement of patients within a plurality of different risk groups 418b comprising a first risk group 420b and a second risk group 422b. The placement of the patients within the plurality of different risk groups 418b is subsequently compared to clinical data 1010 to evaluate the plurality of different risk groups 418b.

FIGS. 11a-11b illustrate exemplary curves showing a survival probability of a plurality of different risk groups of patients that are receiving or that are to receive CDK 4/6 inhibitor therapy for HR+ metastatic breast cancer.

FIG. 11a illustrates exemplary Kaplan Meier curves 1100 showing a survival probability of patients over time for RRS assessment. In the exemplary Kaplan Meier curves 1100 the RRS is computed on pre-treatment imaging data. Low risk patients are represented by a first curve 1102 and high risk patients are represented by a second curve 1104. The calculated radiomic risk scores of the low risk patients illustrated by the first curve 1102 (e.g., patients with a low pre-treatment RRS) corresponds to a high rate of overall survival, while the calculated radiomic risk scores of the high risk patients illustrated by the second curve 1104 (e.g., patients with a high pre-treatment RRS) corresponds to a lower rate of overall survival.

FIG. 11b illustrates exemplary Kaplan Meier curves 1106 showing a survival probability of patients over time for RECIST (Response evaluation criteria in solid tumors) assessment. The exemplary Kaplan Meier curves 1106 utilize assessment over 6 months. Low risk patients are represented by a first curve 1108 and high risk patients are represented by a second curve 1110. The exemplary Kaplan Meier curves 1100 and 1106 show that the survival of patients within both the low risk (first curves 1102 and 1108) and the high risk group (second curves 1104 and 1110) are highly comparable between the RRS (FIG. 11a) and a progress of RECIST assessment (FIG. 11b). Therefore, the exemplary Kaplan Meier curves 1100 and 1106 illustrate that the disclosed radiomic risk scores can generate an accurate prognosis of a patient's response to CDK 4/6 inhibitor therapy before the therapy has begun.

FIG. 12 illustrates some embodiments of a method 1200 of utilizing radiomic heterogeneity features for prognosis of patients that are receiving or that are to receive CDK 4/6 inhibitor therapy for HR+ metastatic breast cancer.

The method 1200 comprises a training phase 1202 and an application phase 1204. The training phase 1202 is configured to determine a plurality of different risk groups. Respective ones of the plurality of different risk groups are associated with a range of radiomic risk scores (RRS) determined using radiomic heterogeneity features. The plurality of different risk groups respectively correspond to expected prognosis in response to CDK 4/6 inhibitor therapy for treatment of HR+ metastatic breast cancer. In some embodiments, the training phase may be performed according to the acts described in relation to FIG. 3.

The application phase 1204 comprises receiving additional imaging data from an additional patient, at 1206. The additional imaging data may comprise radiological data from a CT scan, from a MRI scan, from a PET scan, or the like.

At 1208, an additional lesional mask and an additional perilesional mask are identified from the additional imaging data.

At 1210, additional radiomic heterogeneity features are extracted from the additional lesion and perilesional masks.

At 1212, an additional radiomic risk score (RRS) is determined from the additional radiomic heterogeneity features.

At 1214, the patient is associated with a risk group based upon the additional RRS. For example, based upon the additional risk score the patient may be associated with a first risk group that responds well to CDK 4/6 inhibitor therapy or with a second risk group that does not respond well to CDK 4/6 inhibitor therapy.

At 1216, a treatment plan is determined based upon the risk group that the patient is associated with. For example, if the patient is associated with the first risk group, then the patient will be treated with CDK 4/6 inhibitor therapy. Alternatively, if the patient is associated with the second risk group, then the patient will not be treated with CDK 4/6 inhibitor therapy.

Figure 13:
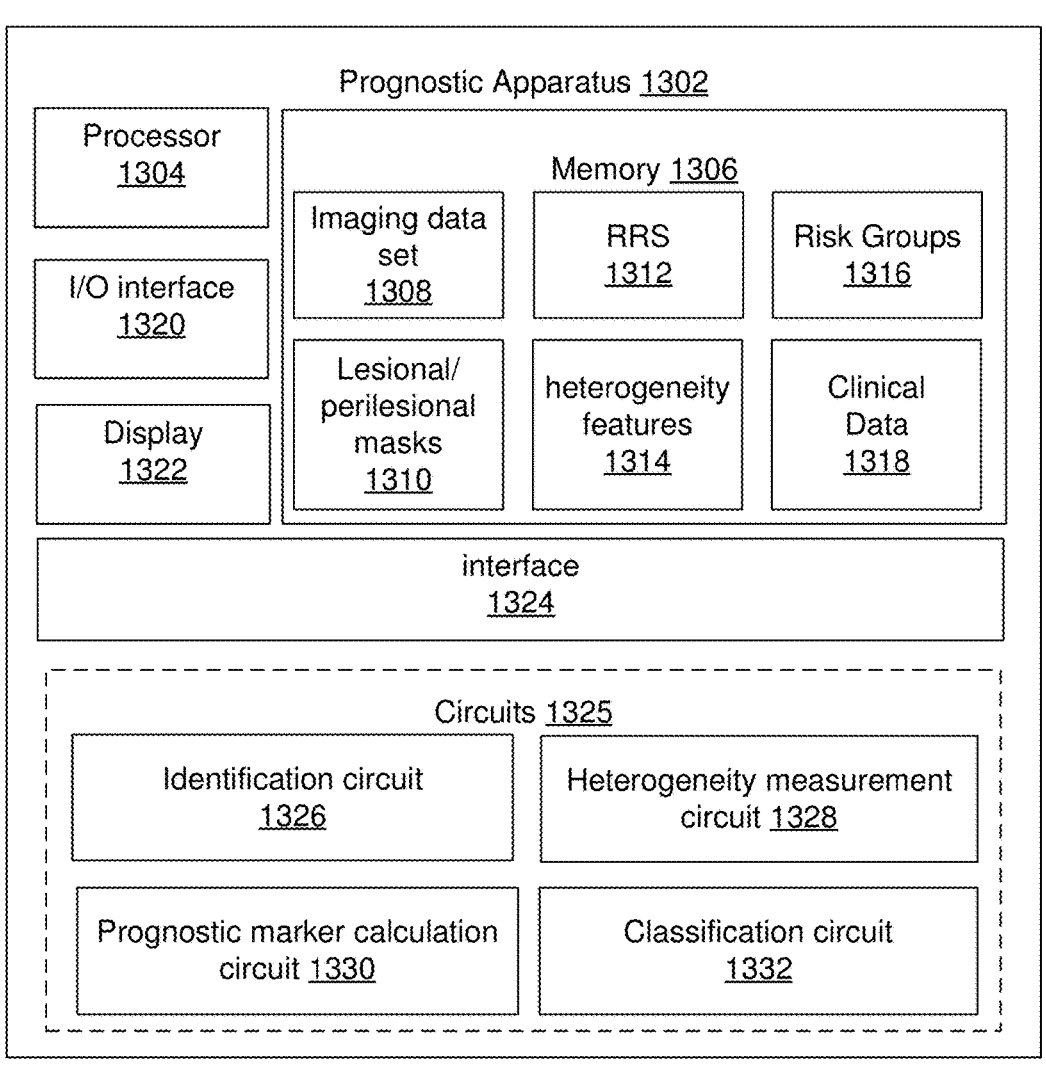
FIG. 13 illustrates some embodiments of a block diagram of an apparatus that is configured to utilize radiomic heterogeneity features from imaging data for prognosis of patients with HR+ metastatic breast cancer.

FIG. 13 illustrates some embodiments of a block diagram of an apparatus 1300 that is configured to utilize radiomic heterogeneity features from imaging data for prognosis of patients with HR+ metastatic breast cancer.

The apparatus 1300 comprises a processor 1304 and a memory 1306. The processor 1304 can, in various embodiments, comprise circuitry such as, but not limited to, one or more single-core or multi-core processors. The processor 1304 can include any combination of general-purpose processors and dedicated processors (e.g., graphics processors, application processors, etc.). The processor(s) 1304 can be coupled with and/or can comprise memory (e.g., memory 1306) or storage and can be configured to execute instructions stored in the memory 1306 or storage to enable various apparatus, applications, or operating systems to perform operations and/or methods discussed herein.

Memory 1306 can be configured to store one or more radiological images 1308 (e.g., CT, MRI, PET, SPECT, ultrasound, etc.) of metastases for a plurality of patients having HR+ metastatic breast cancer. Each of the radiological image(s) can have a plurality of pixels, each pixel having an associated intensity. In some embodiments, memory 1306 can store a training set of images for training a classifier and/or a validation set of images. In some embodiments, the one or more radiological images 1308 may comprise images of liver metastases of patients having HR+ metastatic breast cancer The apparatus 1300 also comprises an input/output (I/O) interface 1320 (e.g., associated with one or more I/O devices), a display 1322, a set of circuits 1325, and an interface 1324 that connects the processor 1304, the memory 1306, the I/O interface 1320, and the set of circuits 1325. I/O interface 1320 can be configured to transfer data between memory 1306, processor 1304, circuits 1325, and external devices, for example, a medical imaging device such as a CT (etc.) system or apparatus. The display 1322 is configured to output or display the prognosis the apparatus 1302.

The set of circuits 1325 can comprise an identification circuit 1326, a heterogeneity measurement circuit 1328, a prognostic marker calculation circuit 1330, and a classification circuit 1332. The identification circuit 1326 is configured to access one or more radiological images (e.g., a training set of images, or an image of a metastasis within a patient for whom a prognosis is to be determined) and to identify lesion and perilesional regions within the images. Accessing the radiological image(s) can comprise accessing radiological image(s) stored in memory 1306. In one embodiment, accessing the radiological image(s) can include accessing radiological image(s) stored in a data storage device, including a hard disk drive, a solid state device, a tape drive, or accessing radiological image(s) over a local area network, or accessing radiological image(s) over the internet. In some embodiments, the identification circuit is configured to delineate (contour) metastases and use the delineated metastases to form images of lesional masks and perilesional masks. In some embodiments, the lesional masks and the perilesional masks may be stored in the memory.

In various embodiments, the heterogeneity measurement circuit 1328 is configured to determine texture features comprising radiomic heterogeneity features 1314 based on the images of lesional masks and perilesional masks 1310. In some embodiment, the heterogeneity measurement circuit 1328 is configured to determine the radiomic heterogeneity features 1314 using a gray level co-occurrence matrix (GLCM). The GLCM measures heterogeneity by measuring how closely associated image signals within a local region are, thereby giving a measure of heterogeneity within a lesion and outside a lesion. In some embodiments, the statistics of GLCM heterogeneity comprise a matrix that is defined over the lesional masks and the perilesional masks 1310.

In various embodiments, the prognostic marker calculation circuit 1330 is configured to determine a radiomic risk score (RRS) 1312 from the radiomic heterogeneity features. In some embodiments, the prognostic marker calculation circuit 1330 may use an elastic net regularized Cox proportional hazards model to derive a radiomic risk score (RRS). In other embodiments, the prognostic marker calculation circuit 1330 is configured to determine a prognostic marker based on a difference between the radiomic heterogeneity features 1314 at different times during treatment (e.g., at pre-treatment and mid-treatment). In some embodiments, the RRS 1312 may be validated utilizing clinical data 1318.

A classification circuit 1332 is configured to classify patients into risk groups 1316 based on their prognostic marker (e.g., their RRS). The classification circuit 1332 may be configured to classify patients into a first group that responds favorably to CDK 4/6 inhibitor therapy, and a second group that responds poorly to CDK 4/6 inhibitor therapy. In some embodiments, the classification circuit

1332 may classify the patients by comparing a RRS of a patient to a risk score threshold. In some embodiments, the risk score threshold may be derived within the training set to stratify the risk score within a plurality of different risk groups (e.g., within a low risk group and a high risk group).

Example Use Case 1

The following discussion provides example embodiments in connection with a first example use case involving a method of utilizing heterogeneity features from imaging data to determine a prognosis of patients that are receiving or that are to receive CDK 4/6 inhibitor therapy for HR+ metastatic breast cancer.

Methodology

From a registry, 46 patients with hormone receptor-positive metastatic breast cancer treated with palbociclib harboring liver metastases prior to drug exposure were identified. Patients were divided at random into equally sized training and testing cohorts. 98% of the patients were females. A median age of the patients at diagnosis was 62. All patients were estrogen receptor-positive (ER+) and 10% were HER2+. 65% of the patients had exposure to palbociclib in the $1^{st}$ or $2^{nd}$ lines of treatment. Patients with objective response/stable disease per RECIST v1.1 were defined as 'responders' (65%), and those with progressive disease were 'non-responders' (35%). 13 radiomic texture features measuring subtle pixel-wise differences in lesion heterogeneity were extracted on pre-treatment CT within the first liver lesion measured for RECIST assessment and a 5 mm surrounding perilesional region. Within the training set, an elastic net-regularized Cox proportional hazards model was constructed to derive the RRS. A risk threshold was also derived in the training set to optimally stratify patients into high and low risk groups. RRS and risk groups were then evaluated for association with overall survival (OS) and response within the testing set.

Results

The RRS consisted of 2 lesion features of the lesion and 3 perilesional features. Heterogeneity of the lesional and perilesional environment was found to be associated with poor outcome. In the independent testing set (n=23), RRS was continuously associated with OS (Hazard Ratio=1.47, p=0.023, c-index=0.68), as were categorical risk groups (p=0.0042, HR=4.13, c-index=0.67). Median survival times in the high and low risk groups were 0.103 and 2.34 years, respectively. RRS and risk groups remained significant in a multivariable comparison with clinical variables and RECIST assessment on post-treatment imaging. When compared directly with RECIST response in the testing set, RRS was found to also be predictive of response with an area under the ROC curve of 0.65.

CONCLUSION

RRS incorporating intra- and perilesional radiomic features could predict overall survival and response prior to initiation of CDK 4/6 inhibitor therapy in MBC with liver metastasis.

Example Use Case 2

The following discussion provides example embodiments in connection with a second example use case involving a method of utilizing heterogeneity features from imaging data to determine a prognosis of patients that are receiving or that are to receive CDK 4/6 inhibitor therapy for HR+ metastatic breast cancer.

Methodology 33 patients with ER+ breast cancer metastasized to the liver who received palbociclib in combination with anti-estrogen therapy were identified from a registry. For each patient, the CT exams were acquired prior to treatment and the first scan following initiation of treatment (median time between scans of 106+/−48.6 days). Liver metastases were manually delineated on all scans with consultation of radiology reports. On each scan, gray level co-occurrence matrix (GLCM) entropy, a computational measure of intra-lesional radiomic heterogeneity, was calculated and averaged across all metastatic lesions and its change over treatment was computed. For comparison, response was also assessed via RECIST v1.1:65% of patients had objective response/stable disease, while 35% had progressive disease on scan following initiation of treatment. Imaging metrics were assessed individually and in a multivariate comparison including clinical features for association with overall survival (OS) via a Cox proportional hazards model.

Results

Change in intra-lesion heterogeneity was associated with OS with a hazard ratio [HR] of 2.82 (p=0.0110). An increase in entropy between the pre-treatment and mid-treatment scans was associated with poorer viability on treatment including CDK inhibitors, indicating that a favorable response can be distinguished by a decrease in intra-lesion heterogeneity. RECIST response was also associated with OS (HR=0.24, p<0.001). In a multivariable comparison with clinical variables, change in GLCM entropy and response per RECIST criteria both demonstrated multivariate significance. Neither the heterogeneity measure on the pre-treatment scans (HR=0.56, p=0.23) nor the mid-treatment scans (HR=1.51, p=0.27) alone were significantly associated with overall survival.

CONCLUSION

The change in lesional heterogeneity on clinical imaging following the initiation of treatment was found to offer independent value in distinguishing patients with favorable survival following CDK 4/6 inhibitor therapy.

Therefore, the disclosed method utilizes intra-lesional radiomic heterogeneity information and perilesional radiomic heterogeneity information to generate a prognostic marker that can distinguish HR+ metastatic breast cancer patients who can achieve long-term survival and durable response following CDK 4/6 inhibitor therapy.

It will be appreciated that the disclosed features illustrated and described above (e.g., in FIGS. 1-12) may be implemented as a method, as a non-transitory computer-readable medium storing computer-executable instructions, and/or as an apparatus in various embodiments.

Examples herein can include subject matter such as an apparatus, a digital whole slide scanner, a CT system, an MRI system, a personalized medicine system, a CADx system, a processor, a system, circuitry, a method, means for performing acts, steps, or blocks of the method, at least one machine-readable medium including executable instructions that, when performed by a machine (e.g., a processor with memory, an application-specific integrated circuit (ASIC), a field programmable gate array (FPGA), or the like) cause the machine to perform acts of the method according to embodiments and examples described herein.

References to "one embodiment", "an embodiment", "one example", and "an example" indicate that the embodiment(s) or example(s) so described may include a particular feature, structure, characteristic, property, element, or limitation, but that not every embodiment or example necessarily includes that particular feature, structure, characteristic, property, element or limitation. Furthermore, repeated use of the phrase "in one embodiment" does not necessarily refer to the same embodiment, though it may.

"Computer-readable storage device", as used herein, refers to a device that stores instructions or data. "Computer-readable storage device" does not refer to propagated signals. A computer-readable storage device may take forms, including, but not limited to, non-volatile media, and volatile media. Non-volatile media may include, for example, optical disks, magnetic disks, tapes, and other media. Volatile media may include, for example, semiconductor memories, dynamic memory, and other media. Common forms of a computer-readable storage device may include, but are not limited to, a floppy disk, a flexible disk, a hard disk, a magnetic tape, other magnetic medium, an application specific integrated circuit (ASIC), a compact disk (CD), other optical medium, a random access memory (RAM), a read only memory (ROM), a memory chip or card, a memory stick, and other media from which a computer, a processor or other electronic device can read.

"Circuit", as used herein, includes but is not limited to hardware, firmware, software in execution on a machine, or combinations of each to perform a function(s) or an action(s), or to cause a function or action from another logic, method, or system. A circuit may include a software controlled microprocessor, a discrete logic (e.g., ASIC), an analog circuit, a digital circuit, a programmed logic device, a memory device containing instructions, and other physical devices. A circuit may include one or more gates, combinations of gates, or other circuit components. Where multiple logical circuits are described, it may be possible to incorporate the multiple logical circuits into one physical circuit. Similarly, where a single logical circuit is described, it may be possible to distribute that single logical circuit between multiple physical circuits.

To the extent that the term "includes" or "including" is employed in the detailed description or the claims, it is intended to be inclusive in a manner similar to the term "comprising" as that term is interpreted when employed as a transitional word in a claim.

Throughout this specification and the claims that follow, unless the context requires otherwise, the words 'comprise' and 'include' and variations such as 'comprising' and 'including' will be understood to be terms of inclusion and not exclusion. For example, when such terms are used to refer to a stated integer or group of integers, such terms do not imply the exclusion of any other integer or group of integers.

To the extent that the term "or" is employed in the detailed description or claims (e.g., A or B) it is intended to mean "A or B or both". When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 110105). While example systems, methods, and other embodiments have been illustrated by describing examples, and while the examples have been described in considerable detail, it is not the intention of the applicants to restrict or in any way limit the scope of the appended claims to such detail. It is, of course, not possible to describe every conceivable combination of components or methodologies for purposes of describing the systems, methods, and other embodiments described herein. Therefore, the invention is not limited to the specific details, the representative apparatus, and illustrative examples shown and described. Thus, this application is intended to embrace alterations, modifications, and variations that fall within the scope of the appended claims.

What is claimed is:

1. A method of determining a prognosis for a patient having metastatic breast cancer, comprising:
receiving imaging data from an image of a patient who is receiving or who is to receive cycline dependent kinase 4 and 6 (CDK 4/6) inhibitor therapy for hormone receptor-positive (HR+) metastatic breast cancer;
identifying a lesional region and a perilesional region of a metastasis within the image, the metastasis located in tissue external to the breast;
extracting lesional radiomic heterogeneity features corresponding to the lesional region and perilesional radiomic heterogeneity features corresponding to the perilesional region from the imaging data associated with the metastasis, wherein the lesional radiomic heterogeneity features comprise a median value of gray level co-occurrence matrix (GLCM) entropy within a lesional mask and the perilesional radiomic heterogeneity features comprise a standard deviation of GLCM contrast within a perilesional mask; and
determining a radiomic risk score from both the lesional radiomic heterogeneity features and the perilesional radiomic heterogeneity features, wherein the radiomic risk score is indicative of a response of the patient to CDK 4/6 inhibitor therapy for HR+ metastatic breast cancer.

2. The method of claim 1, wherein the lesional radiomic heterogeneity features and the perilesional radiomic heterogeneity features are extracted from pre-treatment imaging data of the metastasis.

3. The method of claim 1, comprising:
extracting one or more first lesional radiomic heterogeneity features and perilesional radiomic heterogeneity features from a pre-treatment image of the metastasis;
extracting one or more second lesional radiomic heterogeneity features and perilesional radiomic heterogeneity features from a mid-treatment image of the metastasis; and
determining the radiomic risk score based on a difference between the one or more first lesional radiomic heterogeneity features and perilesional radiomic heterogeneity features and the one or more second lesional radiomic heterogeneity features and perilesional radiomic heterogeneity features.

4. The method of claim 1, wherein the radiomic risk score is calculated by applying a regression model to the lesional radiomic heterogeneity features and the perilesional radiomic heterogeneity features.

5. The method of claim 4, wherein the regression model determines a correlation between the lesional radiomic heterogeneity features and the perilesional radiomic heterogeneity features and an overall survival of the patient.

6. The method of claim 1, further comprising:
determining the radiomic risk score from a first number of the lesional radiomic heterogeneity features and from a second number of the perilesional radiomic heterogeneity features, wherein the first number is different than the second number.

7. The method of claim 1, wherein the metastasis comprises liver tissue.

8. A non-transitory computer-readable medium storing computer-executable instructions that, when executed, cause a processor to perform operations, comprising:
receiving imaging data from an image of a patient that is receiving or that is to receive CDK 4/6 inhibitor therapy for HR+ metastatic breast cancer;
identifying one or more lesional regions and one or more perilesional regions of a metastasis within the imaging data, the metastasis located in tissue external to the breast;
extracting lesional radiomic heterogeneity features from the one or more lesional regions and perilesional radiomic heterogeneity features from the one or more perilesional regions, wherein the lesional radiomic heterogeneity features are identified using a median value of gray level co-occurrence matrix (GLCM) entropy and the perilesional radiomic heterogeneity features are identified using a standard deviation of GLCM contrast;
determining a radiomic risk score from the lesional radiomic heterogeneity features and the perilesional radiomic heterogeneity features of the patient, wherein the radiomic risk score is indicative of a response to CDK 4/6 inhibitor therapy for HR+ metastatic breast cancer; and
arranging the patient into a risk group using the radiomic risk score.

9. The non-transitory computer-readable medium of claim 8, further comprising:
determining the radiomic risk score from a first number of the lesional radiomic heterogeneity features and from a second number of the perilesional radiomic heterogeneity features, wherein the first number is different than the second number.

10. The non-transitory computer-readable medium of claim 8, further comprising:
forming an imaging data set using images from a plurality of patients that are receiving or that are to receive CDK 4/6 inhibitor therapy for HR+ metastatic breast cancer;
extracting additional radiomic features from the images within the imaging data set; and
training a machine learning model using the additional radiomic features, wherein the machine learning model is used to determine the radiomic risk score from the lesional radiomic heterogeneity features and the perilesional radiomic heterogeneity features of the patient.

11. The non-transitory computer-readable medium of claim 8, wherein the radiomic risk score is calculated using an elastic net regularized Cox proportional hazards model.

12. The non-transitory computer-readable medium of claim 8, wherein the metastasis comprises liver tissue.

13. An apparatus that facilitates prognosis of CDK 4/6 inhibitor therapy for a patient having metastatic breast cancer, the apparatus comprising:
a memory configured to store imaging data of a metastasis located in tissue external to the breast from a patient that is receiving or that is to receive CDK 4/6 inhibitor therapy for HR+ metastatic breast cancer;
an identification circuit configured to generate a lesional mask and a perilesional mask of the metastasis;
a heterogeneity measurement circuit configured to extract, from the imaging data, lesional radiomic heterogeneity features based on a median value of gray level co-occurrence matrix (GLCM) entropy within the lesional mask and perilesional radiomic heterogeneity features based on a standard deviation of GLCM contrast within the perilesional mask; and a prognostic marker calculation circuit configured to calculate a radiomic risk score from the lesional radiomic heterogeneity features and the perilesional radiomic heterogeneity features, wherein the radiomic risk score is indicative of a response of the patient to CDK 4/6 inhibitor therapy for HR+ metastatic breast cancer.

14. The apparatus of claim 13, wherein the lesional mask and perilesional mask of the metastasis are generated from pre-treatment imaging data.

15. The apparatus of claim 13, wherein the metastasis comprises liver tissue.

\* \* \* \* \*